United States Patent [19]

Rainey

[11] 4,206,843

[45] Jun. 10, 1980

[54] CAUTERIZING SYSTEM

[76] Inventor: Rhett K. Rainey, Box 1434, San Francisco, Calif. 94149

[21] Appl. No.: 915,588

[22] Filed: Jun. 15, 1978

[51] Int. Cl.$^2$ .................. A61B 10/00; A61M 35/00; B65D 83/00
[52] U.S. Cl. ............................ 206/216; 128/269; 206/210; 206/361; 222/107; 435/295
[58] Field of Search .............. 206/361, 210, 216; 222/107; 128/2 W, 269; 195/139

[56] References Cited

U.S. PATENT DOCUMENTS

| | | | |
|---|---|---|---|
| 3,450,129 | 6/1969 | Avery et al. | 195/139 |
| 3,640,268 | 2/1972 | Davis | 128/2 W |
| 3,757,782 | 9/1973 | Aiken | 222/107 |

Primary Examiner—William T. Dixson, Jr.
Attorney, Agent, or Firm—Glen R. Simmons

[57] ABSTRACT

A self contained disposable cauterizing system for use in cauterizing benign mucous membrane ulcerations, lacerations or fissures. The system includes a swab having an elongated handle with an absorbent swabbing tip on one end of said handle and with a coating of silver nitrate applied to the opposite end of said handle, an elongated flexible plastic tube and matching cap and a frangible ampoule filled with topical anesthetic, which ampoule is fittable in the plastic tube. In use, the portion of the tube where the ampoule is located is squeezed by the physician user, fracturing the ampoule and allowing the topical anesthetic to be absorbed by the absorbent swab tip. The swab is then withdrawn from the tube after the tube cap is removed, with the topical anesthetic end of the swab being applied to the ulceration, laceration or fissure to render the area insensitive to pain and silver nitrate is thereafter applied from the opposite end of the swab to the affected area for cauterization.

10 Claims, 4 Drawing Figures

CAUTERIZING SYSTEM

BACKGROUND OF THE INVENTION AND OBJECTS

The invention relates to a system for cauterization of benine mucous membrane ulcerations, lacerations and fissures.

Heretofore, there has been no cauterization system which brought together in an efficient, attractive unit, the agents and apparatus desirable and necessary for painless treatment of ulcerations, lacerations and fissures as hereinabove noted. It has been the usual practice to apply silver nitrate without any topical anesthetic being preliminarily applied to the affected area. This practice requires the patient to endure the pain associated with cauterization.

The pertinent prior art known to applicant is as follows:

U.S. Pat. No. 3,835,834 issued to Brown, et al. and classified in 128-2;
U.S. Pat. No. 3,923,604 issued to Monaghan and classified in 195-139;
U.S. Pat. No. 3,759,375 issued to Nappi and classified in 206-63. 2R;
U.S. Pat. No. 3,792,699 issued to Tobin, et al. and classified in 128-2W;
U.S. Pat. No. 3,826,259 issued to Bailey and classified in 128-269;
U.S. Pat. No. 3,614,245 issued to Schwartzman and classified in 401-132;
U.S. Pat. No. 3,450,129 issued to Avery, et al. and classified in 128-2;
U.S. Pat. No. 4,036,230 issued to Adams and classified in 128-169; and
and U.S. Pat. No. 1,132,575 issued to Tuttle.

The prior art provides no teaching of a cauterizing unit as provided by applicant's device.

Therefore, it is an object of the present invention to provide a cauterization system having a disposable pack including topical anesthetic and cauterizing agents.

It is a further object of this invention to provide a swab having silver nitrate on one end thereof and absorbent means on the opposite end thereof for the application of a topical anesthetic.

It is a further object of this invention to provide a swab having silver nitrate on one end thereof and absorbent means on the opposite end thereof for the application of a topical anesthetic and further provide an ampoule of topical anesthetic all of which is to be contained in a plastic tube with complimentary cap.

It is a further object of this invention to provide a cauterizing kit including an applicator having silver nitrate deposited on one end thereof with absorbent means on the opposite end thereof accompanied by a frangible ampoule which includes a topical anesthetic with said applicator and ampoule adapted to fit within a tube open at one end with a complimentary cap to cover open end of said tube.

It is a further object of this invention to provide a cauterizing system including means for providing a topical anesthetic preliminary to the use of the cauterizing agent.

It is a further object of this invention to provide a cauterizing kit which includes in addition to the cauterizing agent a topical anesthetic tube used preliminarily to the application of the cauterizing agent.

It is a further object of this invention to provide a cauterizing system having an applicator stick with a coating of silver nitrate on one end thereof and a bulb of absorbent material on the opposite end thereof, a frangible ampoule of topical anesthetic all enclosed in an elongated flexible plastic tube with complimentary cap.

PREFERRED EMBODIMENT OF THE INVENTION

Figure 1:
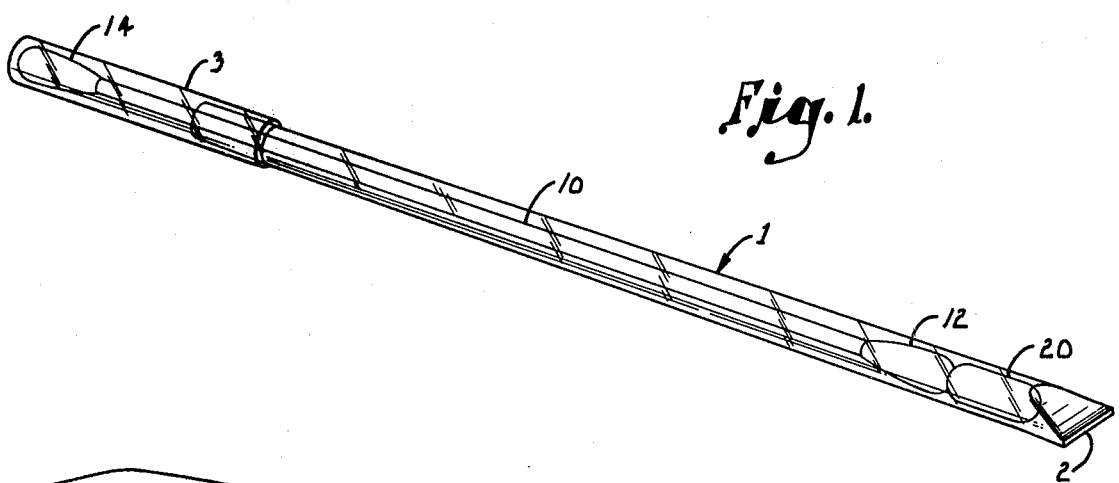
FIG. 1 is a perspective view of the cauterizing unit of the present invention.

Referring now to the FIGS. 1 through 4 there is seen a preferred embodiment of the system or unit of the invention. Specifically, and as seen in FIG. 1, the system includes an elongated plastic enclosure 1, generally round in cross-section except at the lower or righthand end 2 where the tube is sealed as by a stamping or crimping and cutting process. The tube 1 is preferably made of relatively flexible plastic but, of course, could be made of other materials which are inert with respect to silver nitrate.

Tube 1 has a complimentary cap 3 made of material like that of tube 1, which when placed over the end of 1 remote from 2 fits in an air-tight relationship with tube 1. Tube 1 with cap 3 in a closed position as seen in FIG. 1 is on the order of eight inches long but, of course, may be longer or shorter all within the purview of the applicant's invention.

Figure 4:
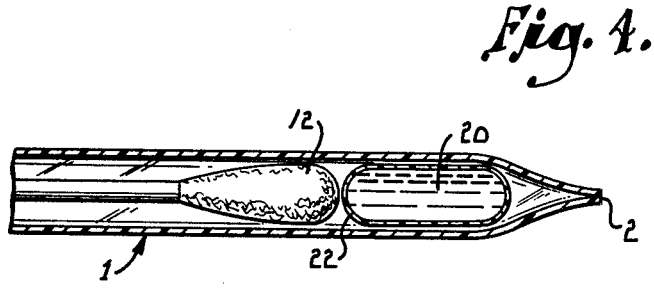
FIG. 4 is and enlarged fragmentary cross-section taken along the longitudinal axis of the lower or righthand end of the cauterizing system as shown in FIG. 1.

As further seen in FIG. 1 enclosed in plastic tube 1 is an elongated swab handle 10 preferably made of wood and on the other of five inches in length and about 3/32 of an inch in diameter. On one end of swab handle 10 is mounted a swab 12 of absorbent material, preferably cotton. At the other end of swab handle 10 there is a coating or bulb 14 of a cauterizing agent such as silver nitrate. Further included within tube 1 is an ampoule or capsule, generally referred to as 20, of a size such that when introduced at the open or top end of tube 1 it slides easily down the tube to the lower righthand end 2. Ampoule or capsule 20 is filled with a topical anesthetic such as viscous lidocanine. Other topical anesthetics which may be used in lieu of viscous lidocaine are viscous xylocaine, xylocaine ointment 2.5% xylocaine ointment - 5%. The anesthetic is encapsulated in a frangible plastic or glass ampoule 22 as shown in FIG. 4. The topical anesthetic is preferably enclosed in the ampoule or capsule 22 to prevent evaporation or other escape preliminary to the time of use.

Thus, it may be seen that the cauterizing system or unit is brought together in an efficient, attractive arrangement whereby an elongated swab handle 10 having a swab or absorbent material 12 on one end with silver nitrate 14 located on the opposite end, along with frangible ampoule 20, are placed within a flexible plastic tube or container 1 and thereafter cap 3 is placed in an air-tight arrangement around the open end of tube 1. The whole unit may, of course, be sealed in a paper or plastic envelope should distribution and transfer to the place of use after the manufacturing process so dictate.

Figure 2:
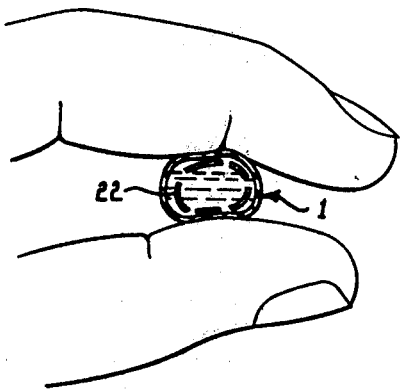
FIG. 2 includes a cross-section of the device at the point of the enclosure tube where the ampoule is located as depicted during the process of fracturing the ampoule by a thumb and forefinger of the human hand.
Figure 3:
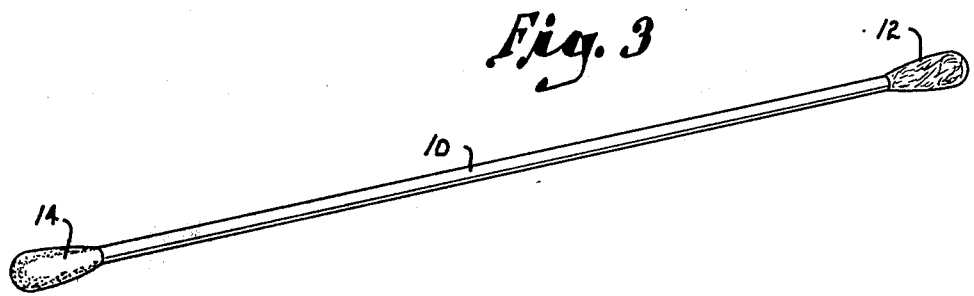
FIG. 3 is a perspective view of the swab handle showing the absorbent material and silver nitrate.

In use the physician or other user of the device grasps the end of tube 1 about the point where said ampoule is located. This squeezing action by the user generally between the thumb and forefinger as depicted in FIG. 2 fractures ampoule 22 without fracturing or perforating the exterior of tube 1. The fracturing of ampoule 22 permits the escape of the lidocaine or other topical anesthetic into the lower or sealed end 2 of tube 1. Either directly or by tipping the tube 1 such that end 2 is higher than cap 3 the topical anesthetic is absorbed to a material extent by swab or absorbent material 12 on the end of handle 10. Upon said absorption, cap 3 of tube 1 is then removed by the user of the cauterization unit thus exposing the upper end of handle 10, the silver nitrate coating 14, to the open atmosphere. The swab device 10, 12, 14 is then removed from tube 1 with the user then directing swab end 12 against the mucous membrane ulceration, laceration or fissure sufficiently to render the affected area insensitive to pain. Thereafter the opposite end of swab handle 10, that is the silver nitrate coated end 14, is then applied by the user to said ulceration, laceration or fissure to cauterize same to the extent deemed necessary by the physician or user. After the cauterization process is finished the device may then be discarded and disposed of in the manner that swab sticks generally are disposed of by medical personnel.

It is, therefore, seen that the applicant's device provides an inexpensive cauterizing system including a provision for applying a topical anesthetic preliminary to the cauterizing process, thus mitigating the amount of pain a patient must endure in order to undergo treatment by cauterization.

It should be further noted that of course, swab handle 10 including the cauterizing agent 14 and cotton tip 12 may be used apart from the container and ampoule 20, i.e. the swab device 10, 12, 14 may be used with topical anesthetic from another and/or larger supply. In other words the swab device 10, 12, 14 could be used in connection with a source of topical anesthetic existing in a physician's office or hospital without limiting the applicant's device to the enclosure and ampoule combination thus providing even further flexibility in use of the novel combination of the swab device having a cauterizing agent deposited on one end thereof with absorbent means on the opposite means thereof.

Having fully described my invention, I claim:

1. In a cauterizing system: swab means including an elongated means having absorbent means on one end thereof and cauterizing means on the other end thereof;
   an elongated container means having an open end and a closed end, said container means being formed of deformable material;
   said swab means being adapted to fit within said elongated container means through said open end;
   ampoule means containing topical anesthetic means adapted to fit within said container, said ampoule means being made of frangible material and adapted when positioned in said container means, to be crushed when the portion of said container means adjacent said ampoule means is squeezed inwardly, thus releasing said topical anesthetic means within said container means whereby said absorbent means absorbs said topical anesthetic means after said ampoule means is crushed;

2. The system of claim 1 wherein said absorbent means is cotton.

3. The system of claim 2 wherein said topical anesthetic is viscous lidocaine.

4. The system of claim 3 wherein said cauterizing means is silver nitrate.

5. The system of claim 4 wherein said elongated means is a wooden stick.

6. The system of claim 5 wherein said container means is plastic.

7. The system of claim 6 further including cap means adapted to fit around and enclose said open end of said elongated container means.

8. The system of claim 1 wherein said cauterizing means is silver nitrate.

9. The system of claim 8 wherein said topical anesthetic means is viscous lidocaine.

10. The system of claim 8 wherein said elongated means is a wooden stick.

* * * * *